(12) United States Patent
Marshall et al.

(10) Patent No.: US 8,491,531 B2
(45) Date of Patent: Jul. 23, 2013

(54) ELECTRICALLY ACTUATED INJECTOR

(75) Inventors: Jeremy Marshall, Oxford (GB); Steven Mark Guy Rolfe, Bicester (GB)

(73) Assignee: Owen Mumford Limited, Oxford (GB)

( * ) Notice: Subject to any disclaimer, the term of this patent is extended or adjusted under 35 U.S.C. 154(b) by 43 days.

(21) Appl. No.: 12/991,308

(22) PCT Filed: May 8, 2009

(86) PCT No.: PCT/GB2009/050489
§ 371 (c)(1),
(2), (4) Date: Mar. 22, 2011

(87) PCT Pub. No.: WO2009/136209
PCT Pub. Date: Nov. 12, 2009

(65) Prior Publication Data
US 2011/0166521 A1    Jul. 7, 2011

(30) Foreign Application Priority Data
May 9, 2008 (GB) .................................. 0808389.1

(51) Int. Cl.
*A61M 5/20* (2006.01)
(52) U.S. Cl.
USPC ........................................ 604/135; 604/232

(58) Field of Classification Search
USPC .......................... 604/134, 135, 157, 187, 232
See application file for complete search history.

(56) References Cited

U.S. PATENT DOCUMENTS

| | | | |
|---|---|---|---|
| 3,695,266 A | 10/1972 | Lussier | |
| 4,313,439 A * | 2/1982 | Babb et al. | 604/28 |
| 5,478,316 A | 12/1995 | Bitdinger et al. | |
| 7,736,344 B2 * | 6/2010 | Moberg et al. | 604/232 |
| 2006/0258986 A1 | 11/2006 | Hunter et al. | |
| 2008/0051727 A1 * | 2/2008 | Moberg et al. | 604/207 |

FOREIGN PATENT DOCUMENTS

| | | |
|---|---|---|
| EP | 0293958 A1 | 12/1988 |
| JP | 2001-187137 A | 7/2001 |
| WO | 97/36623 A1 | 10/1997 |
| WO | 01/85233 A2 | 11/2001 |
| WO | 2004024218 A1 | 3/2004 |

OTHER PUBLICATIONS

International Search Report, dated Jul. 29, 2009, from corresponding PCT application.

* cited by examiner

*Primary Examiner* — Laura Bouchelle
(74) *Attorney, Agent, or Firm* — Young & Thompson

(57) ABSTRACT

An injector 12 includes a plunger 17 for expelling drugs from a cartridge 10 which can be inserted into the injector 12. An actuator 27 is provided for operating an escapement mechanism 21 to control the movement of the plunger under a drive force and hence the expelled drug.

15 Claims, 5 Drawing Sheets

ELECTRICALLY ACTUATED INJECTOR

BACKGROUND OF THE INVENTION

1. Field of the Invention

This invention relates to injectors, such as are used by insulin users.

2. Description of the Related Art

The trend has been to provide those patients who are required to regularly self-inject with automatic injection devices which can provide multiple doses. It is obviously desirable to ensure that the correct dosage volume is delivered each time but the correct dosage volume will vary from patient to patient. It is therefore equally desirable to provide a system which can deliver dose units so that a user can deliver the right number of units for their condition. There are therefore attractions in providing an electronically controlled system but any such system must be fail safe.

Typically injectors are mechanical and work on the basis of a pen like injector into which a disposable drug cartridge can be introduced. The cartridge is arranged to receive a hypodermic needle. With current systems it can be difficult to monitor dose units where a cartridge is not sufficiently full to deliver the whole required dose.

BRIEF SUMMARY OF THE INVENTION

Some or all of these problems may be mitigated by embodiments of the invention set out below.

From one aspect the invention consists an injector for use with a drug cartridge including:

a plunger for movement in a direction for acting, in use, to expel a dose or part thereof from the cartridge;

a power source for acting on the plunger to move it in the direction;

an escapement for acting on the plunger to hold it and release it against the action of the power source to control the movement of the plunger in the direction; and an actuator for moving the escapement between 'release' and 'hold' positions.

The term 'escapement' is used broadly to describe any mechanism which alternately holds and releases an element under the influence of a drive force, whether linear or rotary. The term 'cartridge' is used to describe any arrangement that allows a drug to be expelled from a container, and includes syringes etc.

Although the actuator may comprise an electrical or electro-magnetic actuator such as a solenoid, it is preferred for it to be a piezoelectric actuator. Piezoelectric actuators are very highly controllable by means of applied voltage and are also fast acting. The use of a piezoelectric actuator therefore enables the plunger to be moved forward in very small increments and hence there can be very accurate control of dosage volume. However, if there is any failure in the power supply to the piezoelectric actuator, or extremely unusually, in the actuator itself, the actuator will cease to function and the escapement will hold the plunger against movement in the direction.

Thus the actuator may be energised by a step voltage change, or an electric pulse or pulse train produced by an appropriate pulse generator or oscillator. Because each pulse or change of state supplied to the actuator produces a set small increment of movement of the plunger this makes it possible to exert a high degree of control over the volumetric dose and also the rate of expulsion of the dose, by suitably controlling the number of pulses and their frequency or spacing. In addition, by counting the pulses (and thus increments of movement) the control limit can deduce the actual position of the plunger and so the amount of drug already delivered and the amount still remaining.

The plunger may have a longitudinal ratchet and the escapement may include a co-operating toothed arrangement such as an internally toothed collar arranged for movement transverse to the direction to engage with and disengage from the ratchet. Arrangements other than the collar may of course be used. For example, the plunger may have two parallel inwardly directed ratchets with their teeth facing each other, and the escapement may comprise a toothed escapement member disposed internally between the two ratchets movable alternately between hold and release positions. Still further, the escapement may comprise a profiled track on e.g. the plunger that co-operates with a latch escapement finger that is moved between hold and release positions. The track may be of saw-tooth profile. Preferably the plunger has a pair of transversely opposed, aligned, ratchet surfaces and the collar may have respective tooth portions for engaging respective ratchet surfaces. In that case the teeth of the respective portions are preferably 180° out of step with each other so that if the escapement is oscillated transversely to the direction, the plunger will be caught first by one tooth portion and then the other in incremental steps substantially defined by the tooth pitch spacing. Alternatively, the tooth portions may be exactly aligned and the ratchet surfaces 180° out of step with each other. The piezoelectric actuator may be in the form of a sheet or beam which bends in response to applied voltage and the injector may further comprise a mechanical amplifier interconnecting the actuator and the escapement. Most conveniently this mechanical actuator is in the form of a pivotable lever.

The injector may further include the cartridge, in which case the time taken between release and recapture of the ratchet by the escapement is greater than the minimum time for expelling a drug from the cartridge.

In any of the above cases, the power source may be a spring or an hydraulic motor. If it is a spring it is preferably a constant force spring.

The injector may further include a control for controlling the application of voltage to the piezoelectric actuator. Additionally or alternatively, it may include a touch-sensitive interface/display for allowing the setting of dose units and/or a trigger switch for initiating an injection.

Although the invention has been defined above, it is to be understood it includes any inventive combination of the features set out above or in the following description.

The invention may be performed in various ways and a specific embodiment will now be described, by way of example, with reference to the accompanying drawings, in which:

DETAILED DESCRIPTION OF THE PREFERRED EMBODIMENTS

Figure 1:
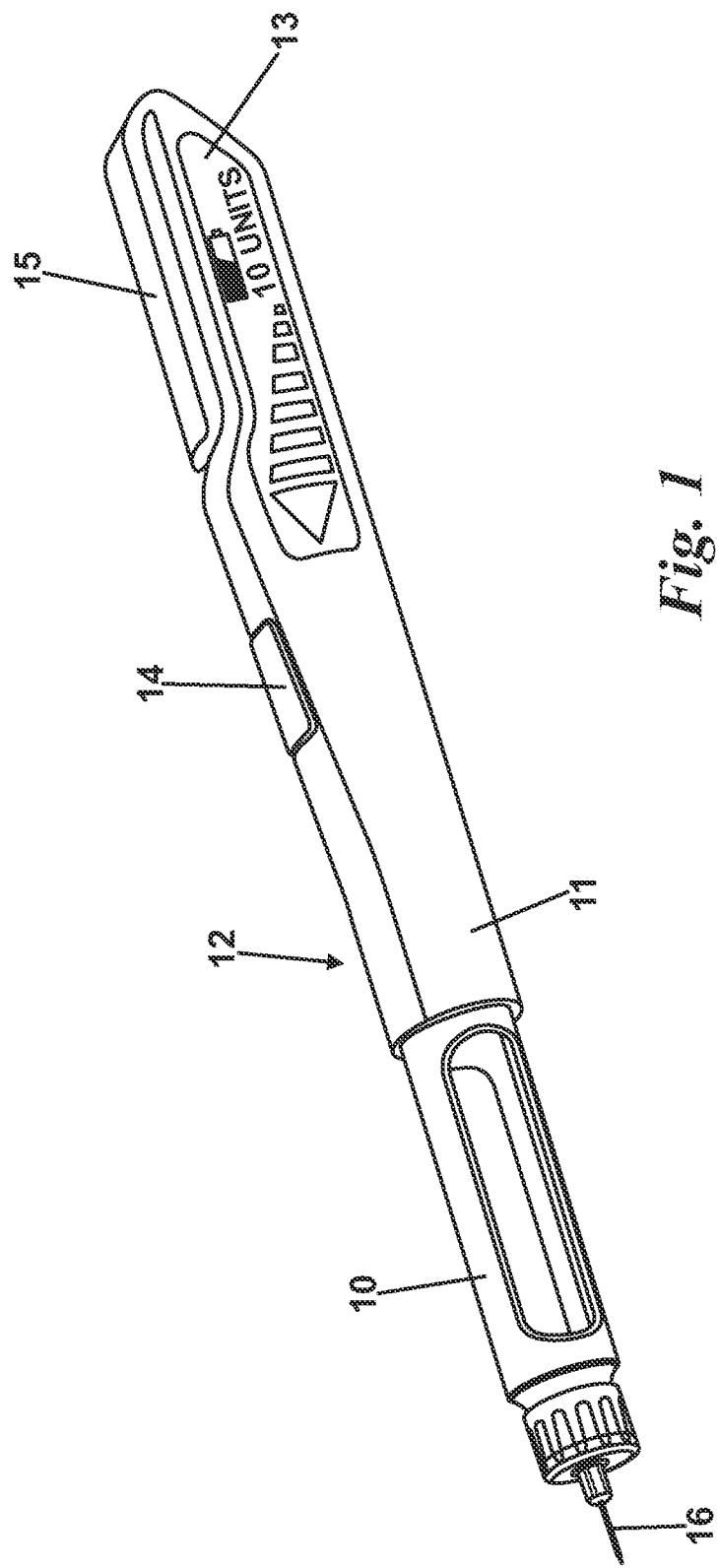
FIG. 1 is an overall view of an injector with a cartridge mounted therein.

In FIG. 1 a cartridge 10 is mounted into the barrel 11 of an injector 12. The injector 12 has a touch-sensitive interactive display 13, and a firing or trigger button 14, 15. A hypodermic needle 16 can be mounted on the cartridge 10 in a known manner.

Figure 2:
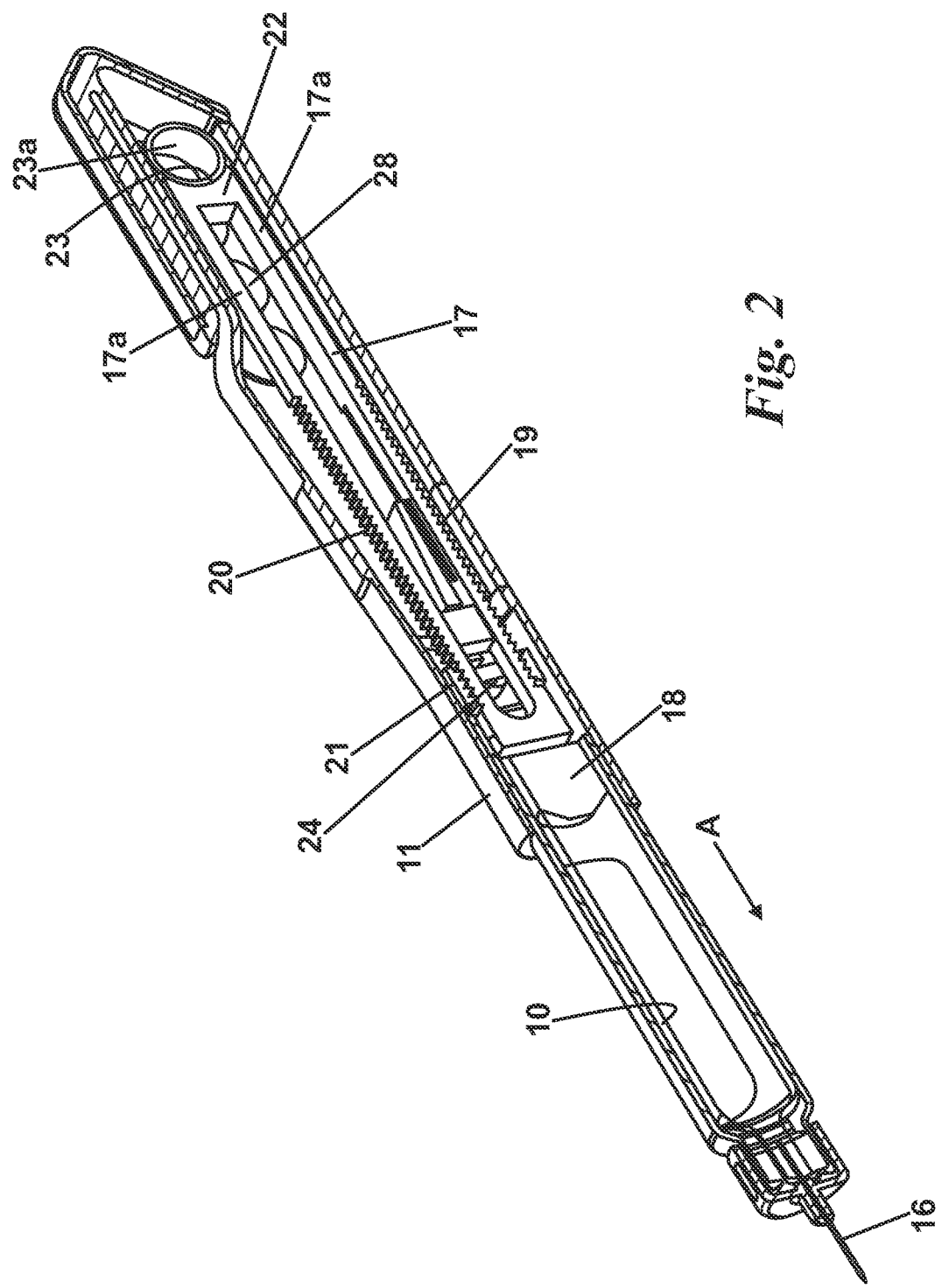
FIG. 2 is a longitudinal section through the injector and cartridge combination of FIG. 1.

Turning to FIG. 2, a plunger 17 extends up most of the length of the barrel 11 cooperates with a piston head 18 slideably located within the cartridge 10, when the latter is mounted in the injector 12. As will readily be appreciated, movement of the plunger 17 and hence the piston 18 in the direction A will cause an amount of the drug contained within the cartridge 10 to be expelled from the needle 11.

The plunger 17 has a pair of elongate struts 17a which carry outwardly facing ratchets having teeth surfaces 19, 20 that engage with corresponding inwardly facing surfaces of an escapement mechanism 21, which will be described in more detail below.

The struts 17a conjoin at an abutment 22 at the clip end of the barrel 11. The abutment 22 forms a curved seat 23 for receiving the coil of a constant force spring 23a which acts between the plunger head 18 and a fixed anchorage on the side wall of the barrel 11 to urge the plunger 17 in the direction A and thereby expel the drug through the hypodermic needle 11. The constant force spring applies a substantial constant force to the plunger throughout the length of its stroke from its outermost position shown in FIG. 2 to a forwardmost position which, after expulsion of the entire contents of the cartridge over several doses, it has driven the piston to the forward end of the cartridge.

This motion is however restricted by the escapement mechanism 21. The escapement mechanism essentially includes a collar 24 which can best be seen in FIGS. 3 and 4. The collar 24 is of open U-shaped form and consists of a back wall and two parallel side walls each of which has a respective inwardly facing collar tooth portion 25, 26 for engaging with respective ratchet surfaces, 20, 19. It will be understood that if the collar 24 is moved up and down in the direction of the arrow B the ratchet teeth surfaces 19 and 20 will be respectively released and engaged in such a manner that the plunger 17 can move forward by one ratchet step.

Figure 3A:
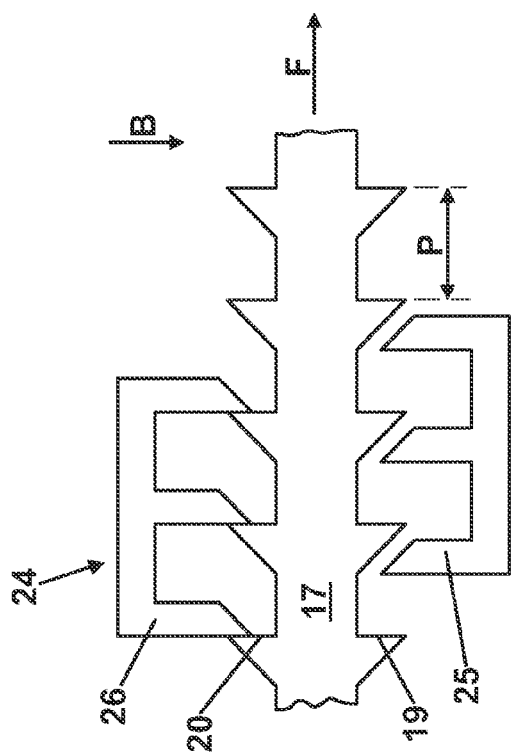
FIGS. 3(*a*) to 3(*d*) are views showing two different escapement configurations.
Figure 3B:
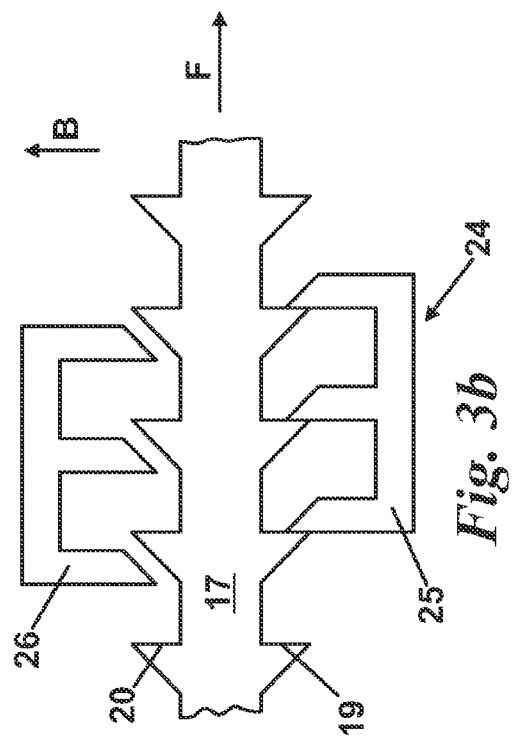
Figure 3C:
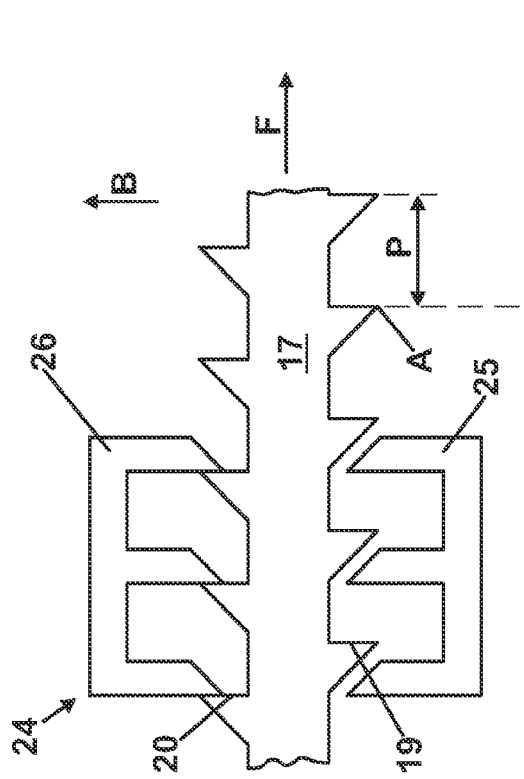
Figure 3D:
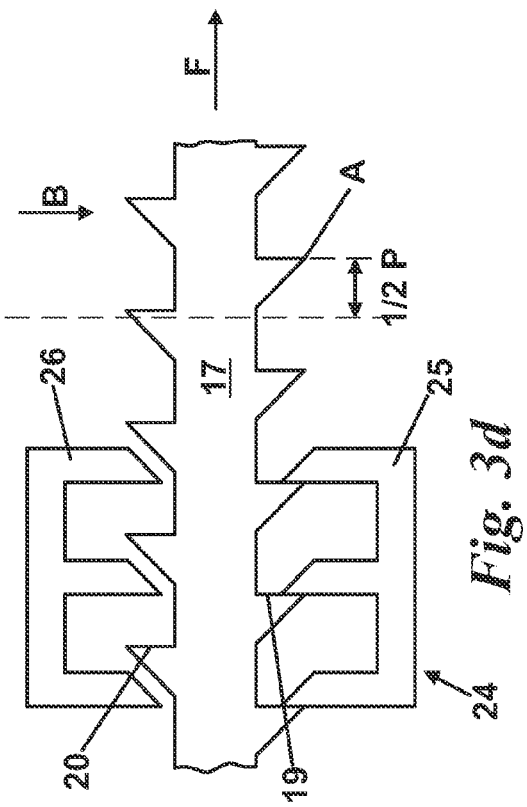
Figure 4:
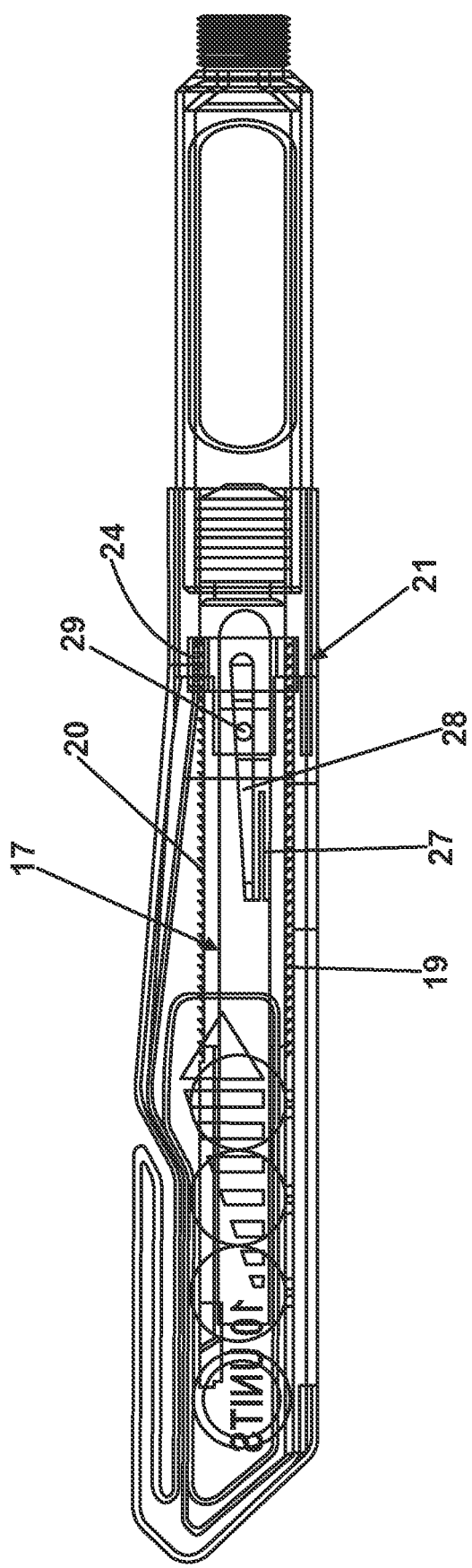
FIG. 4 is a view of the injector of FIGS. 1 and 2 taken from the other side with the internal mechanisms.

In this instance this level of control is particularly obtained by having the teeth of portion 25 offset from those in portion 26 in direction of arrow F by one half of the pitch of the ratchet. This arrangement is shown in FIGS. 3a and 3b. As an alternative, the ratchet teeth surfaces 19 and 20 may be offset by ½ pitch from side to side. This latter arrangement is shown in FIGS. 3c and 3d. In both instances the plunger is advanced by one pitch increment, 'P', for each complete up/down cycle of the cover 24.

The very accurate movement of the collar 24 in this manner can be obtained in this embodiment using a bending piezoelectric actuator 27 which acts on one end of a pivoted lever 28, the other end of which is connected to the collar 24. The pivot can be seen at 29 and it will be noted that it is asymmetrically disposed on the lever 28 so that the relatively small force generated by the piezoelectric actuator 27 is amplified by the mechanical advantage afforded by the lever when it is applied to the collar 24.

By applying a step voltage to the piezoelectric actuator 27 the collar 24 can be oscillated in this manner in a highly controlled fashion so that the plunger will move forward in small steps expelling individual dose increments through the needle 16, with typically several such increments making up a single dose. It will be appreciated that other suitable actuators could be used, such as a solenoid etc.

Figure 5:
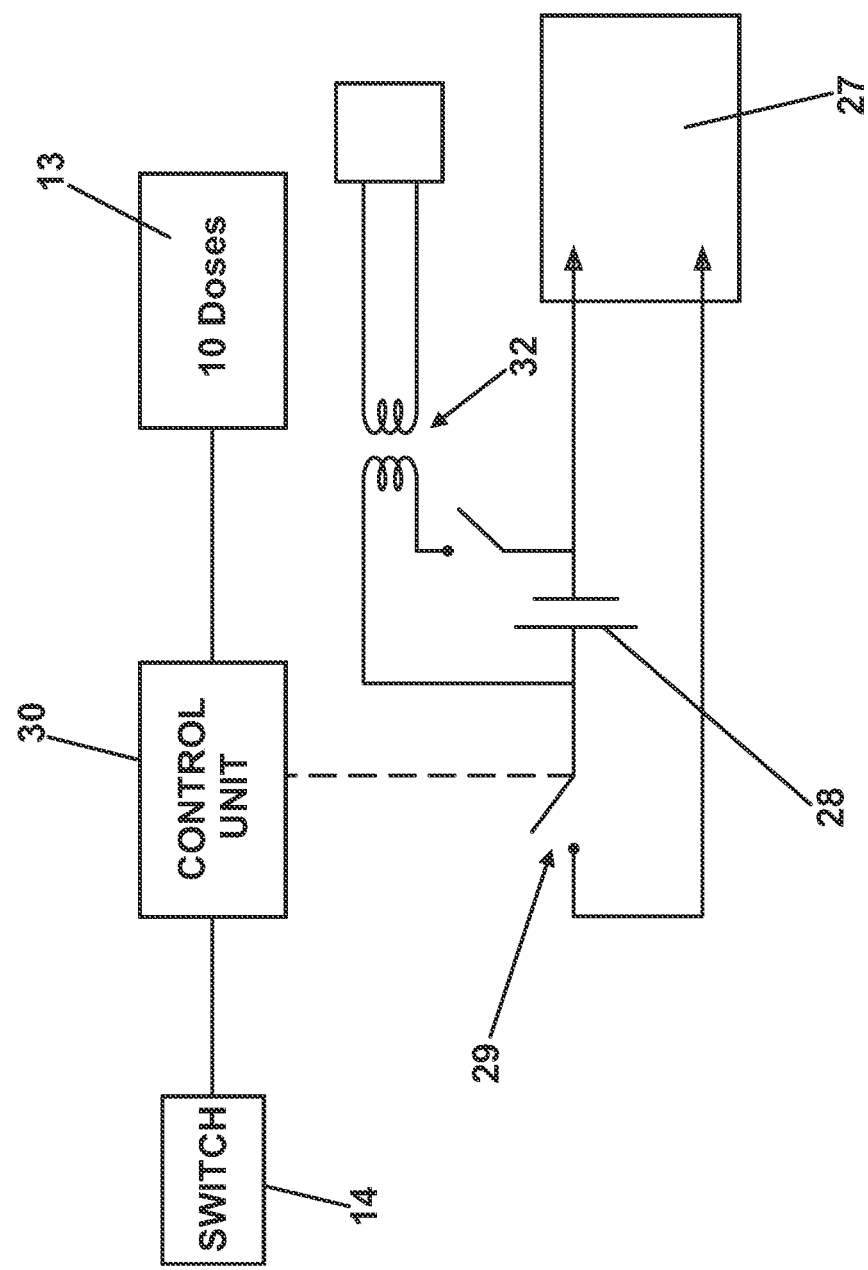
FIG. 5 is a schematic electronic control circuit.

Such control can be obtained using a circuit such a shown in FIG. 5. As can be seen in FIG. 5 voltage can be applied to the actuator 27 from a battery or batteries 28 in accordance with operation of switch 29 under the control of control unit 30.

The control unit 30 is also connected to the interactive display 13 whereby the user can 'dial up' the required dosage volume and then initiate the injection procedure by pressing switch 14. The control 30 then delivers an appropriate number of pulses to the switch 29 causing an appropriate number of oscillations of the actuator 27 and hence the collar 24 allowing the requisite number of stepped forward movements of the plunger 17.

The battery 28 can in fact be a number of lithium cells as indicated in FIG. 2 and a no contact charging system, such as generally indicated at 32 may be provided.

The cartridge 10 is preferably engaged in the barrel 11 by a bayonet fastening. The teeth on the ratchet surfaces 19, 20 face in the opposite direction to the arrow A so that when the cartridge is pushed into the barrel 11, the plunger can be driven back in one movement as the teeth on the ratchet surfaces will cam past the teeth on the collar 24.

It is of course necessary that any movement of the plunger 17 in the direction A is of sufficient duration to overcome the inertia of the liquid drug, because if there is no drug expelled from the cartridge 10 then the plunger 17 cannot actually move. Accordingly, in the described embodiment, the spacing of the teeth on the collar 24, relative to the teeth on the ratchet surfaces 19 and 20 must be such that the time between 'release' and 'hold' is greater than the time taken for the plunger 17 to move sufficiently to expel liquid from the cartridge 10. This can vary in dependence on the features of the drug, cartridge and hypodermic needle, which do not form part of the basic embodiment of the invention and so it may be necessary to specify suitable drug/cartridge combinations for use with a particular injector 12.

Alternatively the time between release and hold may be controlled by an adjustment of the control unit 30, thus tailoring the injector to a specific drug/cartridge/needle combination.

This adjustment could also be used to slow the speed of delivery of a drug by slowing the frequency of the escapement mechanism. This would be useful in the case of drugs which are painful when delivered fast, or when high volumes of drug are being delivered subcutaneously which may take a significant period of time to be absorbed. Likewise, subject to the constraints above, the speed of delivery may be increased, or vary during the expulsion phase.

The invention claimed is:

1. An injector for use with a drug cartridge (10) comprising:
   a plunger (17) for movement in a direction for acting, in use, to expel a dose or part thereof from the cartridge;
   a power source (23a) for acting on the plunger to move it in the direction;
   an escapement (21) for acting on the plunger to hold it, and release it against the action of the power source (23a) to control the movement of the plunger in the direction; and
   a piezoelectric actuator (27) for moving the escapement between 'release' and 'hold' positions;
   wherein the piezoelectric actuator (27) is in the form of a sheet or beam and bends in response to applied voltage, and further comprises a mechanical amplifier (28) interconnecting the actuator and the escapement.

2. The injector as claimed in claim 1, wherein the plunger (17) has a longitudinal ratchet (19, 20) and the escapement includes a toothed member (24) arranged for movement transverse to the direction to engage with and disengage from the ratchet.

3. The injector as claimed in claim 2, wherein the plunger (17) has a pair of opposed ratchet teeth surfaces (19, 20) and the toothed member comprises a collar with respective toothed portions (26, 25) for engaging respective ratchet surfaces (19, 20).

4. The injector as claimed in claim 3, wherein the respective toothed portions (26, 25) of the collar are 180° out of phase with each other.

5. The injector as claimed in claim 3, wherein the teeth on the respective ratchet surfaces (19, 20) are offset ½ pitch side to side.

6. The injector as claimed in claim 1, wherein the mechanical amplifier is a pivoted lever (28).

7. The injector as claimed in claim 1 further including a cartridge (10) and wherein time taken between release and recapture of the ratchet by the escapement (21) is greater than minimum time for expelling a drug from the cartridge.

8. The injector as claimed in claim 1, wherein the power source (23a) is a spring or an hydraulic motor.

9. The injector as claimed in claim 8, wherein the spring is a constant force spring (24).

10. The injector as claimed in claim 1 further including a control (30) for controlling the application of voltage to the piezoelectric actuator.

11. The injector as claimed in claim 10, wherein the control (30) is arranged to control the rate of movement of the plunger in the direction.

12. The injector as claimed in claim 11 including a touch-sensitive interface/display (13) for allowing the setting of dosage volume.

13. The injector as claimed in claim 1 further including a trigger switch (14).

14. The injector as claimed in claim 1, wherein the plunger (17) has a longitudinal ratchet (19, 20) and the escapement includes a toothed member (24) arranged for movement transverse to the direction to engage with and disengage from the ratchet.

15. The injector for use with a cartridge (10) comprising
a plunger (17) co-operable with said cartridge to move in a direction to expel a dose or part thereof,
a power source for acting on the plunger to move it in the direction,
an electrically activated escapement operable to alternately hold and release the plunger against the action of the power source to allow incremental driven advance of the plunger; and
a piezoelectric actuator (27) for moving the electrically activated escapement between 'release' and 'hold' positions;
wherein the piezoelectric actuator (27) is in the form of a sheet or beam and bends in response to applied voltage, and further comprises a mechanical amplifier (28) interconnecting the actuator and the escapement.

* * * * *

UNITED STATES PATENT AND TRADEMARK OFFICE
CERTIFICATE OF CORRECTION

PATENT NO.       : 8,491,531 B2
APPLICATION NO.  : 12/991308
DATED            : July 23, 2013
INVENTOR(S)      : Marshall et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 177 days.

Signed and Sealed this
Eighth Day of September, 2015

Michelle K. Lee
*Director of the United States Patent and Trademark Office*